United States Patent
Perkins et al.

(10) Patent No.: US 11,076,783 B2
(45) Date of Patent: Aug. 3, 2021

(54) MEDICAL MONITORING OPTICAL COMPUTING DEVICE

(71) Applicant: Halliburton Energy Services, Inc., Houston, TX (US)

(72) Inventors: David L. Perkins, The Woodlands, TX (US); Gregory Powers, Spring, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 833 days.

(21) Appl. No.: 15/034,635

(22) PCT Filed: Dec. 30, 2013

(86) PCT No.: PCT/US2013/078226
§ 371 (c)(1),
(2) Date: May 5, 2016

(87) PCT Pub. No.: WO2015/102559
PCT Pub. Date: Jul. 9, 2015

(65) Prior Publication Data
US 2016/0287146 A1    Oct. 6, 2016

(51) Int. Cl.
| | |
|---|---|
| *A61B 5/1455* | (2006.01) |
| *A61B 5/00* | (2006.01) |
| *G01N 21/31* | (2006.01) |
| *G01N 21/84* | (2006.01) |
| *G01N 33/49* | (2006.01) |
| *G01N 33/497* | (2006.01) |
| *A61B 5/145* | (2006.01) |

(52) U.S. Cl.
CPC ........ *A61B 5/1455* (2013.01); *A61B 5/14507* (2013.01); *A61B 5/14546* (2013.01); *A61B 5/441* (2013.01); *A61B 5/6801* (2013.01); *A61B 5/742* (2013.01); *A61B 5/7405* (2013.01); *G01N 21/31* (2013.01); *G01N 21/8483* (2013.01); *G01N 33/49* (2013.01); *G01N 33/497* (2013.01); *G01N 2201/0222* (2013.01)

(58) Field of Classification Search
None
See application file for complete search history.

(56) References Cited

U.S. PATENT DOCUMENTS

| | | |
|---|---|---|
| 2001/0034477 A1 | 10/2001 | Mansfield et al. |
| 2007/0177240 A1* | 8/2007 | Van Beek .......... A61B 5/14532 359/196.1 |
| 2008/0298649 A1 | 12/2008 | Ennis et al. |
| 2009/0198113 A1 | 8/2009 | Rensen et al. |
| 2009/0219539 A1 | 9/2009 | Myrick et al. |
| 2009/0268203 A1 | 10/2009 | Uzunbajakava et al. |
| 2010/0068714 A1 | 3/2010 | Van Herpen et al. |
| 2010/0285082 A1 | 11/2010 | Fernandez |

(Continued)

OTHER PUBLICATIONS

The Multivariate Optical Element Platform—Cirtemo, 2013 http://www.cirtemo.com/pdf/CIRTEMO_Technology_Overview.pdf (Year: 2013).*

(Continued)

*Primary Examiner* — Kaylee R Wilson
*Assistant Examiner* — Jay B Shah
(74) *Attorney, Agent, or Firm* — Haynes and Boone, LLP

(57) ABSTRACT

Various embodiments of optical computing devices utilized in healthcare-related applications.

17 Claims, 4 Drawing Sheets

(56) References Cited

U.S. PATENT DOCUMENTS

| | | | |
|---|---|---|---|
| 2012/0157160 A1 | 6/2012 | Ozcan et al. | |
| 2013/0034842 A1 | 2/2013 | Tunheim et al. | |
| 2013/0287061 A1 | 10/2013 | Freese et al. | |
| 2014/0349257 A1* | 11/2014 | Connor | G16H 20/60 434/127 |
| 2015/0015884 A1* | 1/2015 | Russell | C09K 8/035 356/402 |

OTHER PUBLICATIONS

Cirtemo Blog; Oct. 2013; http://www.cirtemo.com/blog.html#ice (Year: 2013).*

Extended European Search Report for EP 13900844, 8 pages, dated May 15, 2017.

Myrick, "Multivariate Optical Elements Simplify Spectroscopy," *Laser Focus World,* vol. 38, No. 3, Mar. 1, 2002, pp. 91-94.

Haibach, "Precision in Multivariate Optical Computing," *Applied Optics,* Apr. 1, 2004, vol. 43, No. 10, pp. 2130-2140.

Hill, et al. "Construction, Figures of Merit and Testing of a Single-Cell Fluorescence Excitation Spectroscopy System," *Review of Scientific Instruments,* Jan. 1, 2010, vol. 81, No. 1.

International Search Report and The Written Opinion of the International Search Authority, of the Declaration, dated May 6, 2014, PCT/US2013/078226, 13 pages, ISA/US.

Kattenberg, et al., "Systematic Review and Meta-Analysis: Rapid Diagnostic Tests Versus Placental Histology, Microscopy and PCR for Malaria in Pregnant Women," *Malaria Journal,* Oct. 28, 2011, vol. 10, No. 321.

Malaria Control Today, Roll Back Malaria Department, Current World Health Organization Recommendations, Geneva, Switzerland, Mar. 2005.

Myrick, et al. "A Single-Element All-Optical Approach to Chemometric Prediction," *Vibrational Spectroscopy,* 2002, vol. 28, No. 1, pp. 73-81.

Nelson, et al., "Multivariate Optical Computation for Predictive Spectroscopy," *Analytical Chemistry,* Jan. 1, 1998, vol. 70, No. 1, pp. 73-82.

Priore, et al., "A Miniature Stereo Spectral Imaging System for Multivariate Optical Computing," *Applied Spectroscopy,* Mar. 22, 2004, vol. 58, No. 7, pp. 870-873.

Profeta, et al., "Spectral Resolution in Multivariate Optical Computing," *Spectrochimica Acta Part A: Molecular and Biomolecular Spectroscopy,* 2007, vol. 67, No. 2, pp. 483-502.

Simcock, et al. "Precision in Imaging Multivariate Optical Computing," *Applied Optics,* Mar. 1, 2007, vol. 46, No. 7, pp. 1066-1080.

Soyemi, et al. "Design and Testing of a Multivariate Optical Element: The First Demonstration of Multivariate Optical Computing for Predictive Spectroscopy," *Analytical Chemistry,* Mar. 15, 2001, vol. 73, No. 6, pp. 1069-1079.

Soyemi, et al., "Design of Angle-Tolerant Multivariate Optical Elements for Chemical Imaging,"*Applied Optics,* Apr. 1, 2002, vol. 41, No. 10, pp. 1936-1941.

* cited by examiner

MEDICAL MONITORING OPTICAL COMPUTING DEVICE

The present application is a U.S. National Stage patent application of International Patent Application No. PCT/US2013/078226 filed on Dec. 30, 2013, the benefit of which is claimed and the disclosure of which is incorporated herein by reference in its entirety.

FIELD OF THE DISCLOSURE

Embodiments of present disclosure generally relates to optical analysis of samples in the healthcare industry and, more particularly, to a multivariate optical computing device that utilizes Integrated Computational Elements to analyze medical characteristics of samples.

BACKGROUND

The rapid screening of diseases in individuals is paramount in maintaining one's health and minimizing the spread of infectious diseases between individuals. There are many instances where this becomes challenging. For example, in developing countries like The Democratic Republic of Congo, Nigeria and Sudan, there are frequent outbreaks of malaria. The World Health Organization ("WHO") estimated there were 216 million cases of malaria, of which more than 650,000 people died, many of which were pregnant woman and children. In such countries, malaria is the leading cause of morbidity and death. Incredibly there are 100 countries around the globe where malaria creates a burden on health and economic development. HIV/AIDS and Tuberculosis, in addition to malaria, are targeted by WHO as the most important diseases to eradicate.

Early diagnoses of malaria infections are critical, especially in pregnant woman. Children born to infected mothers often suffer from anemia, and can be affected by intrauterine growth retardation. Although light microscopy is the standard for detection of malaria, some forms of malaria can be detected by antigen-based rapid diagnostic tests ("RDTs"). RDTs can be a viable alternative when light microscopy and lab services are unavailable. RDTs are based on one or more specific monoclonal antibodies: Histidine Rich Protein 2 (HRP2), Plasmodium Lactate Dehydrogenase (pLDH) or Aldolase. These antigens-based RDTs are usually presentenced in lateral flow cassettes, dipstick and card formats.

Nevertheless, there are disadvantages associated with conventional RDTs. For example, where prevalence and host immunity is high, RDT results may lead to false positives. For example, RDT test results may erroneously suggest a false positive diagnosis in patients with parasitaemia incidental to another illness. Also, RDTs detect antigens and not parasites; therefore, they may give a positive result for recent but not current parasitaemia. Detection sensitivity of the RDTs is unpredictable, thus decreasing the reliability of the tests. Reasons for poor field sensitivities may include poor manufacture, damage from humidity and temperature, or incorrect handling.

Accordingly, there is a need in the art for a more robust, versatile and reliable rapid-type diagnosis device.

DESCRIPTION OF ILLUSTRATIVE EMBODIMENTS

Figure 1:
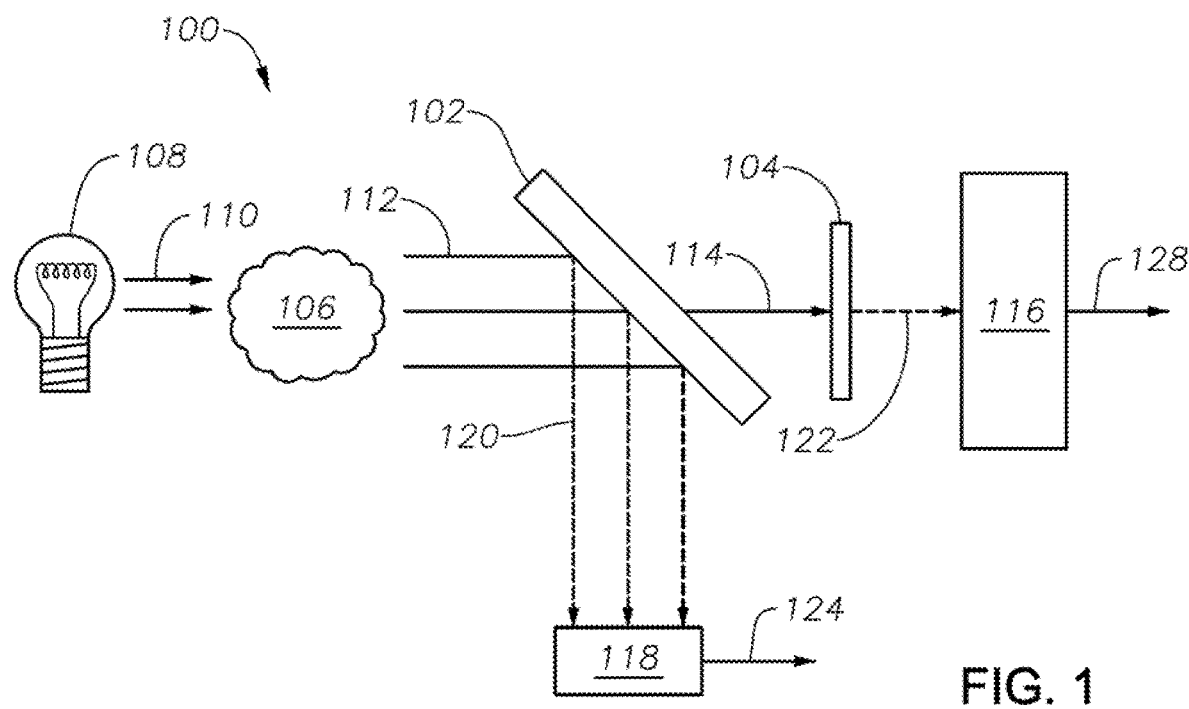
FIG. 1 is a block diagram of an exemplary architecture of an optical computing device employing a transmission mode design, which may be utilized in one or more of the optical computing devices of the present disclosure.

Illustrative embodiments and related methods of the present disclosure are described below as they might be employed in an optical computing device for use in healthcare. In the interest of clarity, not all features of an actual implementation or method are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. Further aspects and advantages of the various embodiments and related methods of the disclosure will become apparent from consideration of the following description and drawings.

As described herein, the present disclosure is directed to an optical computing device having one or more Integrated Computation Element ("ICE") cores to determine various medical characteristics of samples. In certain embodiments, the optical computing device is configured to perform an antigen-based rapid diagnostic test. The sample may be a variety of healthcare-related specimens, such as, for example, blood, urine, stool, skin or eye tissue. Upon analysis of the sample, the optical computing device communicates a medical characteristic of the sample that may indicate the presence of, for example, allergens, parasites, diseases, sugars, enzymes, proteins, or drugs. The communication may take the form of, for example, a visual or audible signal. The optical computing device may be implemented in a variety of ways, such as, for example, a portable device, microfluidic device, viewing device, fiber probe, facial glasses or skin analysis device. These and other advantages of the present disclosure will be apparent to those ordinarily skilled in the art having the benefit of this disclosure.

As will be described herein, illustrative optical computing devices of the present disclosure utilize multivariate optical calculation devices having ICE cores to determine medical characteristics of samples. An optical computing device is a device configured to receive an input of electromagnetic radiation from a substance or sample of the substance and produce an output of electromagnetic radiation from a processing element, also referred to as an optical element. The optical element may be, for example, a narrow band optical element or an ICE core (also known as a Multivariate Optical Element ("MOE")).

Fundamentally, optical computing devices utilize the optical elements to perform regression calculations, as opposed to the hardwired circuits of conventional electronic processors. When light from a light source interacts with a substance, unique physical and chemical information about the substance is encoded in the electromagnetic radiation that is reflected from, transmitted through, or radiated from the sample. Thus, the optical computing device, through use of the ICE core and one or more detectors, is capable of extracting the information of one or multiple characteristics or analytes within a sample and converting that information into a detectable output signal reflecting the overall properties of a sample. Such characteristics may include, for example, the presence of allergens, parasites, or diseases existing within the sample.

FIG. 1 is a block diagram of an exemplary architecture of an optical computing device 100 employing a transmission mode design, which may be utilized in one or more of the optical computing devices of the present disclosure. An electromagnetic radiation source 108 may be configured to emit or otherwise generate electromagnetic radiation 110. As understood in the art, electromagnetic radiation source 108 may be any device capable of emitting or generating electromagnetic, radiation. For example, electromagnetic radiation source 108 may be a light bulb, light emitting device, laser, blackbody, photonic crystal, or X-Ray source, natural luminescence, etc. In one embodiment, electromagnetic radiation 110 may be configured to optically interact with the sample 106 and generate sample-interacted light 112 directed to a beam splitter 102. Sample 106 may be any fluid (liquid or gas), solid substance or material such as, for example, blood, urine, stool, skin tissue, eye tissue, etc.

Sample 106 may be provided to optical computing device 100 through a testing strip of an antigen-based rapid diagnostic test or sample cell, for example, containing sample 106, whereby it is introduced to electromagnetic radiation 110. Alternatively, optical computing device 100 may utilize an optical configuration consisting of an internal reflectance element which analyzes sample 106 through skin tissue as it flows through a blood vessel, or which analyzes the surface of sample 106 (tissue, for example). While FIG. 1 shows electromagnetic radiation 110 as passing through or incident upon the sample 106 to produce sample-interacted light 112 (i.e., transmission or fluorescent mode), it is also contemplated herein to reflect electromagnetic radiation 110 off of the sample 106 (i.e., reflectance mode), such as in the case of a sample 106 that is translucent, opaque, or solid, and equally generate the sample-interacted light 112.

After being illuminated with electromagnetic radiation 110, sample 106 containing an analyte of interest (a medical characteristic of the sample) produces an output of electromagnetic radiation (sample-interacted light 112, for example). As previously described, sample-interacted light 112 also contains spectral information of the sample used to determine one or more medical characteristics of sample 106. Ultimately, a multivariate optical calculation device forming part of device 100 analyzes this spectral information to determine the desired medical characteristic of sample 106. Although not specifically shown, one or more spectral elements may be employed in optical computing device 100 in order to restrict the optical wavelengths and/or bandwidths of the system and, thereby, eliminate unwanted electromagnetic radiation existing in wavelength regions that have no importance. As will be understood by those ordinarily skilled in the art having the benefit of this disclosure, such spectral elements can be located anywhere along the optical train, but are typically employed directly after the light source which provides the initial electromagnetic radiation.

Although not shown, optical computing device 100 may be coupled to a remote power supply, while in other embodiments optical computing device 100 comprises an on-board battery. Optical computing device 100 may also comprise a signal processor (not shown), communications module (not shown) and other circuitry necessary to achieve the objectives of the present invention, as will be understood by those ordinarily skilled in the art having the benefit of this disclosure. It will also be recognized that the software instructions necessary to carry out the objectives of the present invention may be stored within storage located on optical computing device 100 or loaded into that storage from a CD-ROM or other appropriate storage media via wired or wireless methods.

Alternatively, however, the processor may be located remotely from optical computing device 100. In such embodiments, a communications link provides a medium of communication between the processor and optical computing device 100. The communications link may be a wired link, such as, for example, a fiber optic cable. Alternatively, however, the link may be a wireless link. In certain exemplary embodiments, the signal processor controls operation of optical computing device 100. Optical computing device 100 may also include a transmitter and receiver (transceiver, for example) (not shown) that allows bi-directional communication over a communications link in real-time. In certain exemplary embodiments, optical computing device 100 will transmit all or a portion of the medical characteristic data to a remote processor for further analysis. However, in other embodiments, such analysis is completely handled by optical computing device 100 and the resulting data is then transmitted remotely for storage or subsequent analysis. In either embodiment, the processor handling the computations may, for example, analyze the characteristic data, or perform simulations based upon the characteristic data, as will be readily understood by those ordinarily skilled in the art having the benefit of this disclosure.

Still referring to the exemplary embodiment of FIG. 1, beam splitter 102 is employed to split sample-interacted light 112 into a transmitted electromagnetic radiation 114 and a reflected electromagnetic radiation 120. Transmitted electromagnetic radiation 114 is then directed to one or more optical elements 104. Optical element 104 may be a variety of optical elements such as, for example, one or more narrow band optical filters or ICE cores arranged or otherwise used in series in order to determine the characteristics of sample 106. In those embodiments using ICE cores, the ICE core may be configured to be associated with a particular medical characteristic of sample 106 or may be designed to approximate or mimic the regression vector of the characteristic in a desired manner, as would be understood by those ordinarily skilled in the art having the benefit of this disclosure. Additionally, in an alternative embodiment, optical element 104 may function as both a beam splitter and computational processor, as will be understood by those same ordinarily skilled persons.

Nevertheless, transmitted electromagnetic radiation 114 then optically interacts with optical element 104 to produce optically interacted light 122. In this embodiment, optically interacted light 122, which is related to the medical characteristic or analyte of interest, is conveyed to detector 116 for analysis and quantification. Detector 116 may be any device capable of detecting electromagnetic radiation, and may be generally characterized as an optical transducer. For example, detector 116 may be, but is not limited to, a thermal detector such as a thermopile or photoacoustic detector, a semiconductor detector, a piezo-electric detector, charge coupled device detector, video or array detector, split detector, photon detector (such as a photomultiplier tube), photodiodes, local or distributed optical fibers, and/or combinations thereof, or the like, or other detectors known to those ordinarily skilled in the art. Detector 116 is further configured to produce an output signal 128 in the form of a voltage that corresponds to the medical characteristic of the sample 106. In at least one embodiment, output signal 128 produced by detector 116 and the characteristic concentration of the sample 106 may be directly proportional. In other embodiments, the relationship may be a polynomial function, an exponential function, and/or a logarithmic function.

Optical computing device 100 includes a second detector 118 arranged to receive and detect reflected electromagnetic radiation and output a normalizing signal 124. As understood in the art, reflected electromagnetic radiation 120 may include a variety of radiating deviations stemming from electromagnetic radiation source 108 such as, for example, intensity fluctuations in the electromagnetic radiation, interferent fluctuations (for example, dust or other interferents passing in front of the electromagnetic radiation source), combinations thereof, or the like. Thus, second detector 118 detects such radiating deviations as well. In an alternative embodiment, second detector 118 may be arranged to receive a portion of the sample-interacted light 112 instead of reflected electromagnetic radiation 120, and thereby compensate for electromagnetic radiating deviations stemming from the electromagnetic radiation source 108. In yet other embodiments, second detector 118 may be arranged to receive a portion of electromagnetic radiation 110 instead of reflected electromagnetic radiation 120, and thereby likewise compensate for electromagnetic radiating deviations stemming from the electromagnetic radiation source 108. Those ordinarily skilled in the art having the benefit of this disclosure will realize there are a variety of design alterations which may be utilized in conjunction with the present invention.

Although not shown in FIG. 1, in certain exemplary embodiments, detector 116 and second detector 118 may be communicably coupled to a signal processor (not shown) on-board optical computing device 100 such that normalizing signal 124 indicative of electromagnetic radiating deviations may be provided or otherwise conveyed thereto. The signal processor may then be configured to computationally combine normalizing signal 124 with output signal 128 to provide a more accurate determination of the medical characteristic of sample 106. However, in other embodiments that utilized only one detector, the signal processor would be coupled to the one detector. Nevertheless, in the embodiment of FIG. 1, for example, the signal processor computationally combines normalizing signal 124 with output signal 128 via principal component analysis techniques such as, for example, standard partial least squares which are available in most statistical analysis software packages (for example, XL Stat for MICROSOFT® EXCEL®; the UNSCRAMBLER® from CAMO Software and MATLAB® from MATHWORKS®), as will be understood by those ordinarily skilled in the art having the benefit of this disclosure. Thereafter, the resulting data is then transmitted to the processor for further operations.

Figure 2:
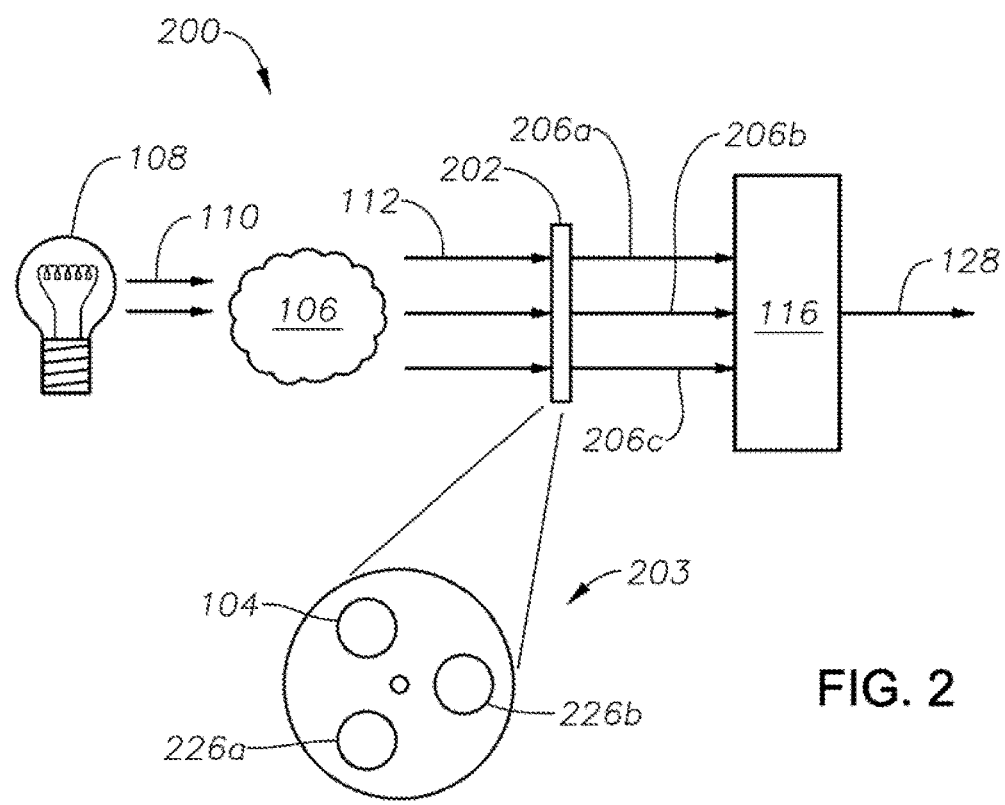
FIG. 2 is a block diagram of an exemplary architecture of an optical computing device employing a time domain mode design, which may be utilized in one or more of the optical computing devices of the present disclosure.

FIG. 2 is a block diagram of an exemplary architecture of an optical computing device 200 employing a time domain mode design, which may be utilized in one or more of the optical computing devices of the present invention. Optical computing device 200 is somewhat similar to optical computing device 100 described with reference to FIG. 1 and, therefore, may be best understood with reference thereto, where like numerals indicate like elements. Optical computing device 200 may include a movable assembly 202 having at least one optical element 104 and two additional optical elements 226a and 226b associated therewith. As illustrated, the movable assembly 202 may be characterized at least in one embodiment as a rotating disc 203, such as, for example, a chopper wheel, wherein optical elements 104, 226a and 226b are radially disposed for rotation therewith. FIG. 2 also illustrates corresponding frontal views of the moveable assembly 202, which is described in more detail below.

Those ordinarily skilled in the art having the benefit of this disclosure will readily recognize, however, that movable assembly 202 may be characterized as any type of movable assembly configured to sequentially align at least one detector with optically interacted light and/or one or more optical elements. Each optical element 104, 226a and 226b may be similar in construction to those as previously described herein, and configured to be either associated or disassociated with a particular characteristic of the sample 106. Although three optical elements are described, more or less optical elements may be employed along movable assembly 202 as desired.

In certain exemplary embodiments, rotating disc 203 may be rotated at a frequency of about 0.1 RPM to about 30,000 RPM. In operation, rotating disc 203 may rotate such that the individual optical elements 104, 226a and 226b may each be exposed to or otherwise optically interact with the sample-interacted light 112 for a distinct brief period of time. Upon optically interacting with the sample-interacted light 112, optical element 104 is configured to generate optically interacted light 206a (a first beam, for example), optical element 226a is configured to generate a second optically interacted light 206b (a second beam, for example) and optical element 226b is configured to generate a normalized electromagnetic radiation 206c (a normalization beam, for example). Detector 116 then receives each beam 206a-c and thereby generates a first, second and third output signal, respectively (output signal 128 comprises the first, second and third signals). Accordingly, a signal processor (not shown) communicatively coupled to detector 116 utilizes the output signal to computationally determine the medical characteristics.

Moreover, in certain exemplary embodiments, detector 116 may be configured to time multiplex beams 206a-c between the individually-detected beams. For example, optical element 104 may be configured to direct first beam 206a toward the detector 116 at a first time T1, optical element 226a may be configured to direct second beam 206b toward the detector 116 at a second time T2, and optical element 226b may be configured to direct third beam 206c toward detector 116 at a third time T3. Consequently, detector 116 receives at least three distinct beams of optically-interacted light which may be computationally combined by a signal processor (not shown) coupled to detector 116 in order to provide an output in the form of a voltage that corresponds to the characteristic of the sample, as previously described. In certain alternate embodiments, beams 206a-c may be averaged over an appropriate time domain (for example, about 1 millisecond to about 1 hour) to more accurately determine the characteristic of sample 106. As previously described, detector 116 is positioned to detect first, second and third beams 206a-c in order to produce output signal 128. In this embodiment, a signal processor (not shown) may be communicably coupled to detector 116 such that output signal 128 may be processed as desired to computationally determine the characteristic of sample 106.

Those ordinarily skilled in the art having the benefit of this disclosure realize the aforementioned optical computing devices are exemplary in nature, and that there are a variety of other optical configurations which may be utilized. These optical configurations not only include the reflection, absorption or transmission methods described herein, but can also involve scattering (Raleigh & Raman, for example) as well as emission (fluorescence, X-ray excitation, etc., for example). The foregoing optical computing devices may be implemented in a variety of ways, including, for example, an on-site medical testing machine, compact device, hand-held devices or other portable devices.

Also note that, as described herein, a "multivariate optical calculation device" forms part of the optical computing device. Note, however, that in some illustrative embodiments the multivariate optical calculation device and optical computing device are one in the same. Alternative, however, the multivariate optical calculation device may only comprise optical elements 104 and 226, detectors 116/118 and the necessary processing circuitry to determine the medical characteristic of sample 106.

Figure 3A:
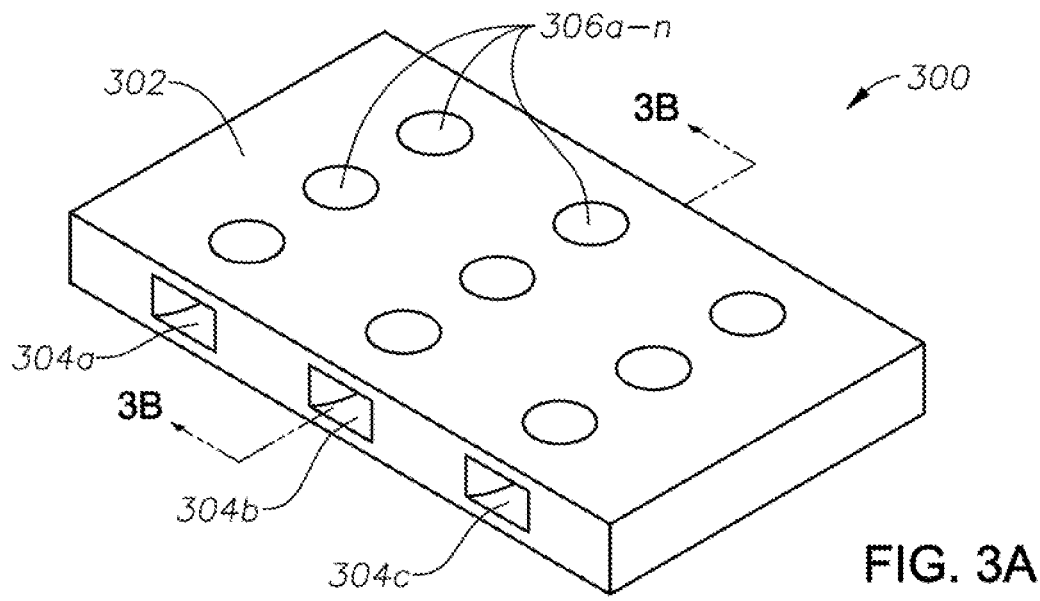
FIG. 3A is a three-dimensional illustration an optical computing device having a multivariate optical calculation device for use in a rapid diagnostic testing device, according to certain illustrative embodiments of the present disclosure.

Now that two illustrative architectures of optical computing devices have been described, various alternative methods of which to implement those architectures will now be described. In certain illustrative embodiments, the optical computing device may be embodied in a portable device, such as an antigen-based rapid diagnostic test ("RDT") device. FIG. 3A is a three-dimensional illustration an optical computing device 300 having a multivariate optical calculation device for use in an RDT device, according to certain illustrative embodiments of the present disclosure. As previously described herein, the multivariate optical calculation device utilizes at least one ICE core to perform regression calculations to thereby determine medical characteristics of samples.

Optical computing device 300 includes a body 302 having matrices of channels 304a-c extending there-through in which to receive a test strip (e.g., RDT strip) or fluid sample. When a test strip is used, health-related specimens (blood or tissue, for example) may be applied to the test strip and then inserted into channels 304. Alternatively, however, health related fluid specimens (blood, urine, other fluids) may be introduced to channels 304 using a variety of methods, as would be understood by those ordinarily skilled persons described herein. Nevertheless, other embodiments may contain more or less channels 304. A plurality of detectors 306a-n are positioned along a surface of device substrate 302 such that the axis of each detector 306 transverses its respective channel 304.

In certain embodiments, optical computing device may be a microfluidic device. In such embodiments, body 302 would be a device substrate and may comprise any number of additional valves, reservoirs, pumps, mixers, etc., necessary to perform device functions, such as volume expansion. The pressure of the exterior of the substrate may be increased or decreased to ease the restrictions on components such as valves or volume constrictions. In certain other illustrative embodiments, channels 304 may comprise a number of additional valves positioned there along so that the volume of fluid injected into channels 304 may be altered as desired.

Figure 3B:
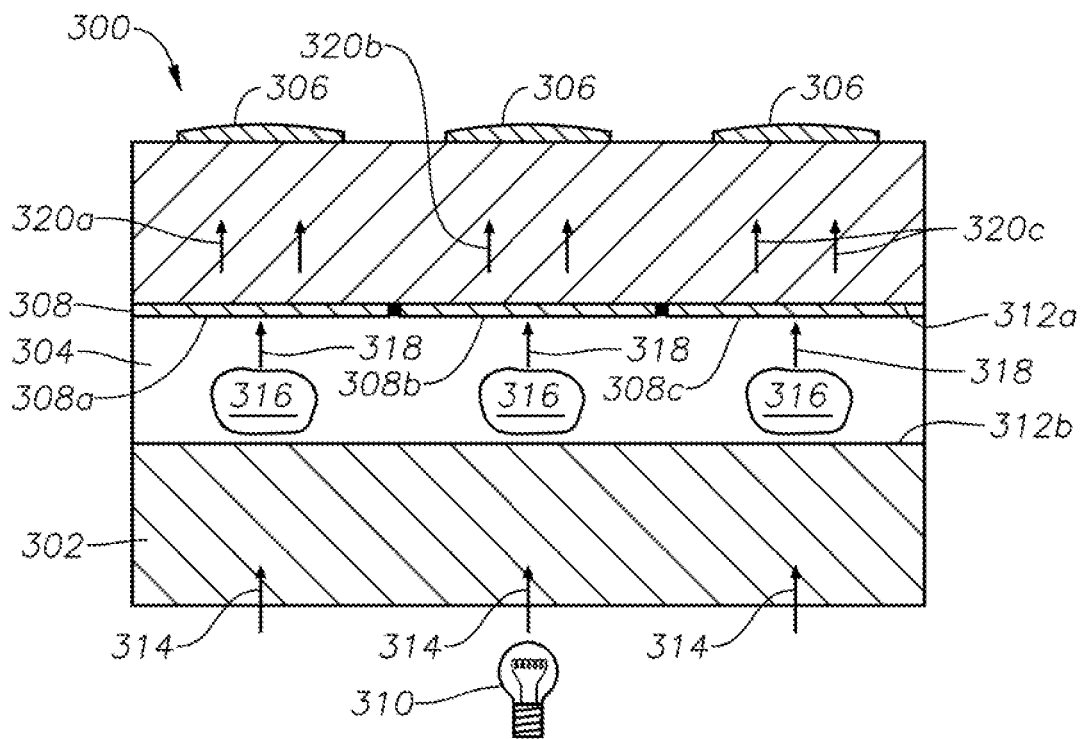
FIG. 3B is a schematic sectional representation of the optical computing device of FIG. 3A along line 3B, according to one illustrative embodiment of the present disclosure.

FIG. 3B is a schematic sectional representation of optical computing device 300 along line 3B of FIG. 3A, according to one illustrative embodiment of the present disclosure. In this example, optical computing device 300 includes a multivariate optical calculation device having one or more light sources 310, an ICE core 308 and detectors 306. The optical calculation device is integrated into body 302 to thereby perform a regression calculation on light emanating from sample 316 (e.g., an RDT test strip or fluid sample) to thereby produce a signal that corresponds to one or more medical characteristics of the sample. In the embodiment of FIGS. 3A and 3B, ICE core 308 is deposited onto the inside surface of a first side 312a of channel 304. In alternate embodiments, however, ICE core 308 may be deposited on both sides of channel 304 or on a second side 312b of channel 304. Moreover, although not shown, light sources 310 may be formed on substrate 302 or the electromagnetic radiation may be provided from some external source.

During fabrication, optical computing device 300 may be made in two parts which, when assembled, form channels 304. As such, the ICE core 308 would be deposited onto one or both sides 312 of channel 304 using a deposition technique. A variety of deposition techniques may be utilized, such as, for example, ion assisted e-beam PVD deposition, as will be understood by those ordinarily skilled in the art having the benefit of this disclosure. Alternatively, the ICE core may be deposited using Atomic Layer Deposition ("ALD"), which is a chemical vapor deposition technique. Use of ALD would allow optical computing device 300 to be formed as one monolithic device. In this example, ICE core 308 may also be deposited by liquid chemical deposition, followed by solvent extraction (evaporation).

Referring to FIG. 3B, ICE core 308 is comprised of multiple ICE cores 308a-c positioned side-by-side in a direction parallel to the axis of channel 304. Alternatively, however, ICE core 308 may comprise only one ICE core. Use of more than one ICE core will allow the measurement of more than one analyte (i.e., medical characteristic) present within sample 316 positioned along channel 304. Note that manufacturing of this embodiment would require split channel fabrication since masking would be necessary to deposit the multiple ICE cores. As shown, each ICE core 308a-c has its own detector 306 to analyze and quantify light emanating from the corresponding ICE core. Thus, the number of detectors 306 is contingent upon the number of ICE cores 308. Detectors 306 may be any device capable of detecting electromagnetic radiation, and may be generally characterized as an optical transducer, as understood in the art. Detectors are further configured to produce an output signal (not shown) in the form of a voltage that corresponds to the particular property of sample 316. Lastly, one or more broadband electromagnetic radiation sources 310 are positioned opposite detectors 306 to produce light to cover the detector array area.

Figure 3C:
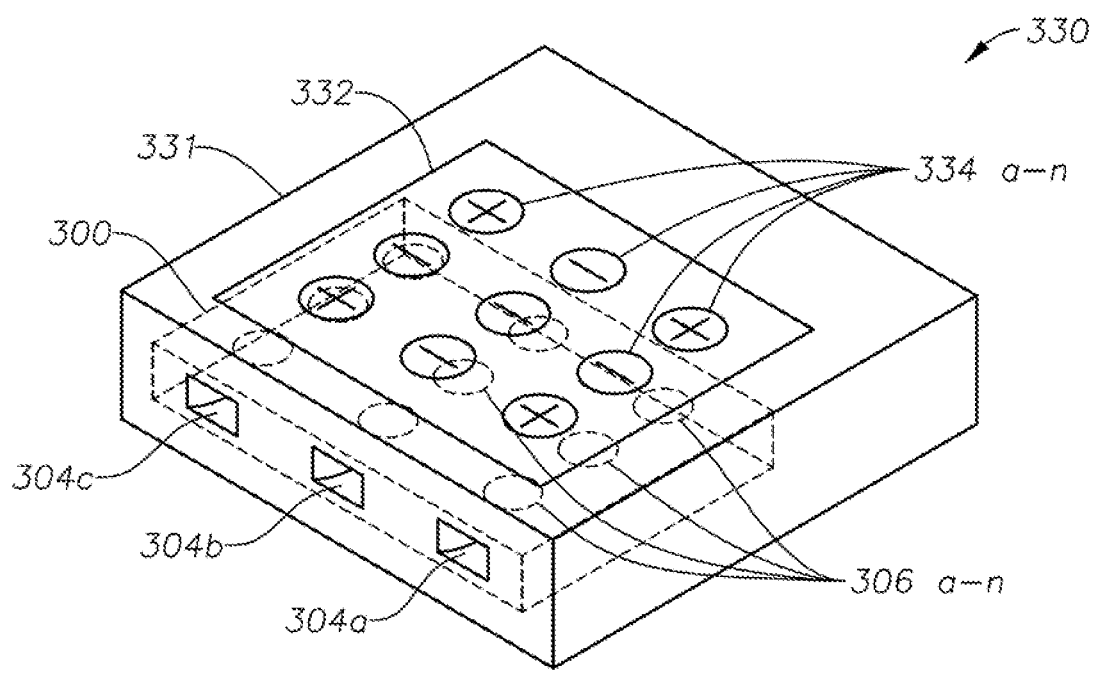
FIGS. 3C and 3D are simplified illustrations of rapid diagnostic testing devices, according to illustrative alternative embodiments of the present disclosure.

FIG. 3C is a simplified illustration of an RDT device 330 utilizing optical computing device 300, according to an illustrative embodiment of the present disclosure. RDT device 330 includes a housing 331 having a display 332 to visually display medical characteristic data (e.g., the results of the testing). In this example, multiple samples 316 may be tested in parallel using an RDT testing strip or by introducing a fluid sample to channels 304 of optical computing device/multivariate optical calculation device 300. With reference to FIGS. 3A-3C, during operation of RDT device 330, an RDT test strip or fluid sample may be introduced to channels 304. Thereafter, electromagnetic source(s) 310 produce electromagnetic radiation 314 which emanates through the optical transparent device substrate 302 to optically interact with sample 316 present in channel 304. After being illuminated with electromagnetic radiation 314, sample 316 containing an analyte of interest (a medical characteristic of the sample, for example) produces an output of electromagnetic radiation (sample-interacted light 318, for example). Sample-interacted light 318 is then directed to ICE cores 308a, b and c, each being designed to approximate or mimic the regression vector of a medical characteristic within sample 316, to thereby produce corresponding optically-interacted light 320a-c. In this embodiment, optically interacted light 320a-c, which is related to a medical characteristic of interest, is conveyed to detectors 306 for analysis and quantification. Detectors 306 are further configured to produce an output signal (not shown) in the form of a voltage that corresponds to the particular medical characteristic(s) of sample 316.

Ultimately, processing circuitry on-board RDT device 330 analyzes the spectral information of the output signal to determine the medical characteristic of interest. For example, the medical characteristic may indicate the presence of allergens, parasites, diseases, sugars, enzymes, proteins or drug in sample 316. Although not specifically shown, one or more spectral elements may be employed in optical computing device 300 in order to restrict the optical wavelengths and/or bandwidths of the system and, thereby, eliminate unwanted electromagnetic radiation existing in wavelength regions that have no importance. As will be understood by those ordinarily skilled in the art having the benefit of this disclosure, such spectral elements can be located anywhere along the optical train, but are typically employed directly after the light source which provides the initial electromagnetic radiation.

The processing circuitry may then display the testing results via display 332. For example, display 332 may include a plurality of icons 334a-n, each corresponding to an ICE core 308—detector 306 pair. Furthermore, each ICE core 308 may be tailored to detect a different medical characteristic, such as, for example, one ICE core detects the presence of HIV in the sample, while others may detect the presence of Malaria, Leishmaniasis, Oncoeherciasis, Schistosomiasis or Lymphatic Filariasis. Accordingly, the corresponding icon 334 may then display a "+" or "−" to indicate the presence or lack thereof of the medical characteristic respectively. In alternative embodiments, the medical characteristic may be communicated audibly via an alert signal, using colors, or any other desired visual, vibrational, or audible alert mechanism, in addition to remote transmission of the medical characteristic data to another computer station, as will be understood by those ordinarily skilled in the art having the benefit of this disclosure.

Note also that alternative embodiments of optical computing device 300 may be utilized with the present disclosure. For example, channels 304 may have differing shapes and sizes or the ICE cores may be position along all sides of the channels. In addition, channels 304 may be sized to accept lateral flow cassettes, dipsticks or card formats typically utilized with conventional RDTs. In yet other embodiments, optical computing device 300 may also include control columns to verify whether the device is working properly. Such alterations will be understood by those ordinarily skilled in the art having the benefit of this disclosure.

Figure 3D:
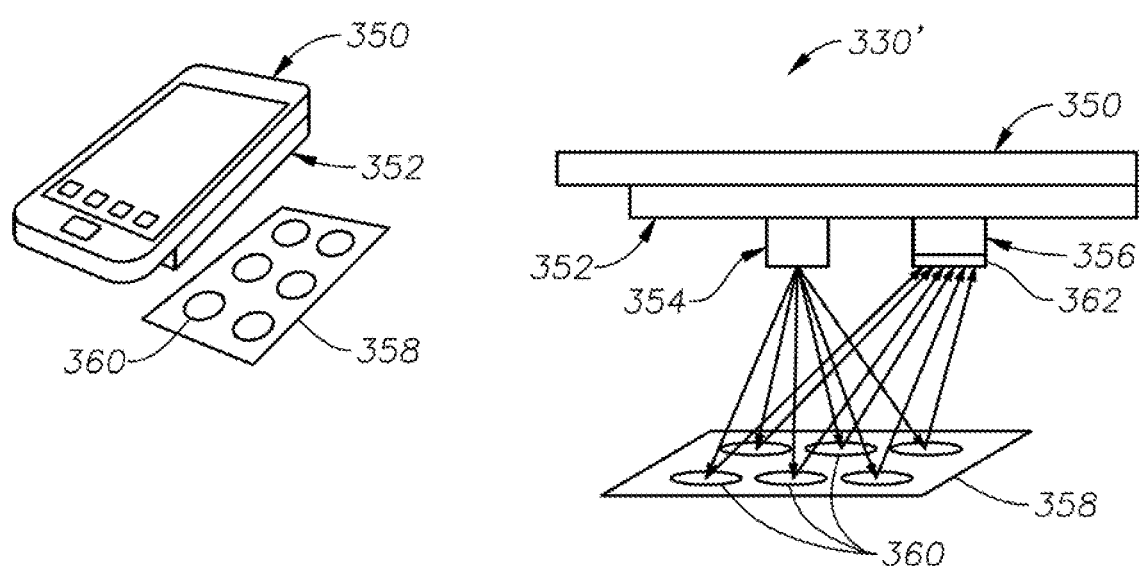

FIG. 3D illustrates an alternative embodiment of RDT device 330. In this example, RDT device 330' is illustrated in 3D (left side) and a 2D sectional view (right side). RDT device 330' includes an analyzer 350, which embodies the system processing circuitry, storage, communications, etc. For example, analyzer 350 may be a handheld device such as a PDA, cellphone, or other computer processing unit. A sensor array 352 is attached to analyzer 350 and operationally coupled thereto. Sensor array 352 contains one or more electromagnetic radiation sources 354 and detectors 356, as previously described herein. Thus, analyzer 350 and sensor array 352 may also be referred to as the optical computing device. Nevertheless, during operation, radiation sources 354 produce light which optically interacts with RDT test strip 358 (containing one or more medical samples 360), which thereby produces sample-interacted light. The sample-interacted light thereafter reflects back to one or more ICE core(s) 362 (forming part of detectors 356), whereby optically-interacted light is produced. The optically-interacted light is then detected by detectors 356, as previously described herein.

Figure 4:
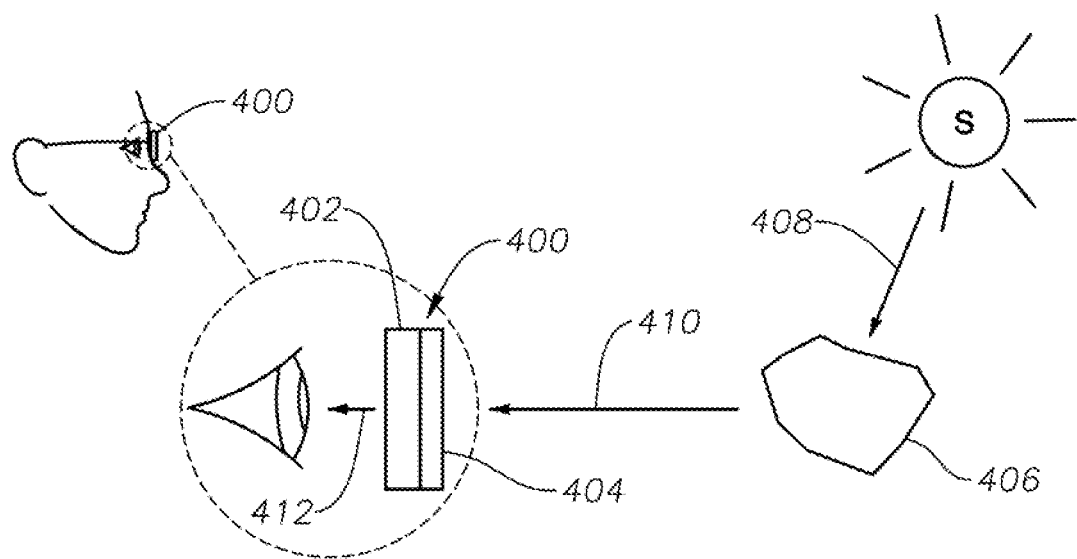
FIG. 4 is a cross-sectional view of a viewing device comprising an optical computing device, according to certain embodiments of the present disclosure.

In certain other illustrative embodiments, the optical computing devices described herein may be embodied in a viewing device such as, for example, facial glasses or some other portable viewing device. FIG. 4 is a 3D and exploded 2D cross-sectional view of a viewing device 400 comprising a multivariate optical calculation device, according to certain embodiments of the present disclosure. In this example, viewing device 400 includes a viewing optic 402, such as, for example, lenses on a pair of facial glasses or some other transparent substrate through which the eye may view. One or more transparent ICE core(s) 404 have been attached (deposited, for example) to optic 402.

During use, sample 406 optically interacts with electromagnetic radiation 408 from an external light source, such as the sun. Alternatively, the electromagnetic radiation may be provided by some other source such as a man-made light source. Nevertheless, this interaction produces sample-interacted light 410, which then optically-interacts with ICE core(s) 404 to produce optically-interacted light 412 which is visible to the eye through transparent optic 402. Here, sample-interacted light 410 is filtered by ICE core(s) 404 such that an optical signature of sample 406 is visible through optic 402. Unlike other embodiments described herein, viewing device 400 utilizes the human eye as the detector. ICE core(s) 404 in device 400 are designed to allow a visual interpretation of the optically interacted light by detection using the human eye and interpretation by the human brain. The human eye-brain function in the same manner as the detector and computer in device 330' described above, as will be understood by those ordinarily skilled in the art having the benefit of this disclosure. Since ICE core(s) 404 are designed to be associated with some medical characteristic (presence of an allergen, for example), the optical signature may be visible to the eye in a number of ways, as mentioned below.

The illustrative embodiments of viewing device 400 may have various applications. For example, the viewing lens could be used to detect food or environmental allergens, such as, the presence of egg, pork, shellfish, soy, diary, or peanuts in food sample or on the surface of other items. In such applications, a food sample may be viewed through the lens to determine if certain allergens are present. The ICE core utilized will be configured for the visible light range, thus able to distinguish the allergens from the complex backgrounds. Also, the ICE core may be coupled with staining and fluorescent detection/discrimination spectroscopic techniques. As a result, if allergens are present, the food item may appear highlighted, color-coded, or otherwise distinguished from the background when viewed through the viewing optic. Alternatively, the viewing device may be embodied in, for example, a handheld device.

In yet other illustrative embodiments, the viewing device may be operationally coupled to a display and associated circuitry. In such embodiments, after the allergen has been detected, device circuitry may quantify an amount of the allergen which is present within the food sample. The quantified amount may then be displayed, along with the specified allergen. Since the ICE cores may be designed to detect any variety of medical characteristics, a single viewing device may be configured to detect one or many allergens. Moreover, in yet other embodiments, the viewing device may be utilized to detect a variety of other substances in the environment or on surfaces, such as, for example, warfare chemical agents.

Figure 5:
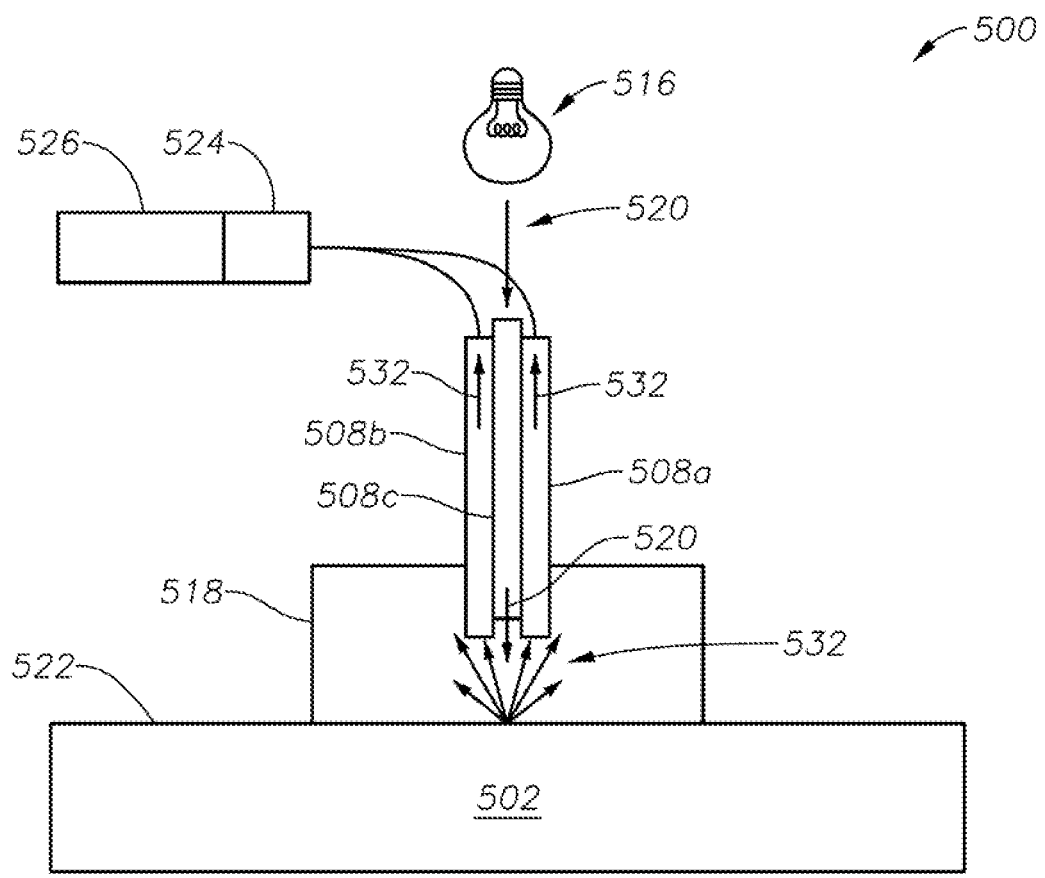
FIG. 5 is a block diagram of a skin analysis device applied to skin tissue, according to certain embodiments of the present disclosure.

In yet another illustrative embodiment, the optical computing device forms part of a skin analysis device. FIG. 5 illustrates a skin analysis device 500 applied to skin tissue, according to certain embodiments. Skin analysis device 500 is an optical computing device which may be applied to skin tissue 502 using a variety of methods, such as, for example, as a watch-like device worn on the skin or a device which may be applied to the skin when testing is desired. Nevertheless, in this example, skin analysis device 500 utilizes diffuse reflectance to detect the medical characteristics of the sample (which may be skin 502 itself or blood, fat cells, nerves, sweat glands, etc. present within skin 502). The diffuse reflectance type system would promise penetration depths of 50-2200 microns to allow interrogation of the dermis, which contain blood vessels.

Optical computing device 500 includes a housing cavity 518 positioned against the surface 522 of skin 502. Fiber optics 508a, b and c extend into housing cavity 518 to communicate electromagnetic radiation to and from housing cavity 518. An ICE core 524 is optically coupled to housing cavity 518 via fiber optics 508a and 508b, whereby a detector detects the optically-interacted light propagating from ICE core 524, as previously described. Lines are shown between fiber optics 508a,b and ICE core 524 for simplicity, as the fiber optic extends all the way between the components.

As previously described, detector 526 is responsive to the output of ICE core 524 for generating an electrical intensity output signal whose value corresponds to a medical characteristic of skin 502 (or other sample resident within skin 502) being determined, as previously described herein. Power may be supplied to electromagnetic radiation source 516 via an on-board power source. A conductor may receive the detector output signal produced by detector 526, and transmit it to an on-board signal processor (not shown) for determining the medical characteristic of skin 502 manifested by the signal on the conductor. The signal processor may then communicate the medical characteristic data in a variety of ways, such as, for example, displaying it via a display (not shown) forming part of skin analysis device 500 or over some communications link, for example wired or wireless, optical, or through near field communication (not shown) to another processing station for further analysis.

Still referring to FIG. 5, during operation of skin analysis device 500, electromagnetic radiation 520 is transmitted via fiber optic 508c to the surface 522 of skin 502. Electromagnetic radiation 520 will penetrate the surface 522 a few micrometers, e.g., 0.3-5 microns. Reflected light 532 (i.e., sample-interacted light) from the surface 522 is collected and is directed to the ICE core 524 via fiber optic 508a and b, where it then passes through ICE core 524 (to produce optically-interacted light) to detector 526, where one or more signals are generated that correspond to the medical characteristic(s) detected in skin 502. It should be understood that a second detector (not shown) may also be responsive to reflected light from ICE core 524 and supplied to a further conductor (not shown) and signal processor for further processing of medical characteristics.

Through use of skin analysis device 500, a variety of the advantages that are provided. For example, when the device is worn on the skin, blood flowing through the veins may be monitored for any number of medically related situations. For example, skin tone maladies may be detected directly or secondary indicators of skin tone maladies may be detected. Alternatively, RDT device 330' of FIG. 3D may be utilized as a skin analysis device. In such an embodiment, instead of analyzing RDT test strip 358 as previously described, RDT device 330' is applied to (or adjacent to) skin 502, and skin 502 is then analyzed for medical conditions.

In another illustrative embodiment of the present disclosure, the optical computing devices described herein may also be used to determine if an individual RDT is damaged by temperature or humidity prior to use. With regard to water damage, the medical characteristic determined by the optical computing device will be the presence of an amount of water affected components within the sample (e.g., RDT test strip, fluid, etc.). With regard to temperature, the analyzed medical characteristics will be the presence of temperature affected components present in the sample. If the optical computing device determines there is water humidity or temperature damage to the sample, the computing device may be configured to correct for such effects. Alternatively, the optical computing device may be configured to signal that the RDT should be discarded if the temperature or water damage is larger than a predetermined threshold.

In certain illustrative embodiments which determine whether an RDT is temperature/humidity damaged, a series of RDTs will be exposed to varying amounts of water damage by exposing them to water vapor at various times and temperatures. Optical spectra will be recorded on the individual components of the RDT (elements in the array) and then each RDT exposed to a test sample that has the representative disease (i.e. malaria). An unaffected RDT will indicate the presence of the disease. When the RDT is affected by water or temperature, however, the RDT may fail to indicate the presence of the disease. A correlation to the optical spectra recorded on the series of RDTs with that of the indication (i.e., yes or no malaria) is analyzed. The correlation analysis may show that a certain quantitative absorption of water (i.e. 100 ppm H2O) is enough to render the RDT ineffective for screening for malaria in a 95% confidence limit. Alternatively, the presence of water may change the enzymes that are used to indicate the presence of malaria to something else and is apparent in the optical spectrum. Either way, certain embodiments of the present disclosure include ICE core(s) designed to determine whether the RDT is defective due to water/temperature damaged, and the results could be used to decide whether to discard the RDT or to qualify the result (e.g., more than 95% confident that the test is accurate for malaria (whether positive or not)).

Furthermore, the optical computing devices may be used to correct for chemical interferents in samples, which would allow use of heretofore unusable RDTs. Here, for example, assume that an RDT gives a visible indication of either a positive or negative indication of a particular medical condition. For example, the indication is a green (for +) or red (for −) on a gray background. Also assume that damage to the RDT results in the degradation of the color change, either when (+) or (−). For example, the color change is shifted to yellow for both cases. Then either a yellow (+ or −) will appear on exposure to the disease. If the process described above is utilized (i.e., collecting spectra on a series of exposed RDTs), and an analysis shows discrimination in a different spectral region (i.e., near infrared), then what would appear as a failed RDT could actually be used by adding an ICE core. This would allow normally discarded RDTs to be used in cases where supply of unaffected RDTs is low.

Therefore, similar tests as those described above could be used to develop an ICE sensor solution to move the otherwise damaged indication to other wavelengths (i.e. infrared) where the RDT indication could be salvaged. In another example, a water/temperature correction ICE is developed to monitor the RDT in parallel with normal methods (ICE or otherwise). If water/temperature damage is present, it is quantified by the computing device and used to correct the signal coming from the normal monitored signal. For example, the mathematics applied by the computing device here would be $Signal_{corr} = Signal_{ICE1} - Signal_{H2O} - Signal_{Temp}$, where $Signal_{corr}$ denotes the corrected signal, $Signal_{ICE1}$ denotes the normal ICE signal, $Signal_{H2O}$ denotes the water damaged signal, and $Signal_{Temp}$ denotes the temperature damaged signal. By subtracting those water/temperature damaged signals from the normal ICE signal, the RDT can be salvaged despite its water/temperature damage.

As described herein, there are a variety of other medical related applications of the present disclosure. The optical computing devices may be used to directly monitor medical characteristics for screening purposes or full diagnostics. The samples may take a variety of forms, such as blood, urine, stool, skin, or eye tissue. Illustrative applications may include using the optical computing device in conjunction with a dialysis machine. Here, the optical computing device may be positioned along the dialysis line carrying the blood. As the blood (i.e., sample) flows through the line, it may be analyzed by the optical computing device, and various medical characteristics determined in real-time. In another example, an optical computing device may form part of a breathalyzer machine. As a user blows into the machine, the optical computing device would analyze the breath particles (i.e., sample) to determine the presence of, for example, alcohol or sugar.

Moreover, the illustrative optical computing devices described herein may be used to monitor chemical species in the background matrix of the body. Using blood or urine as the sample, such chemical species (i.e., medical characteristics) may be sugars, enzymes (including glucose), steroids, drugs (pharmaceutical and illicit), protein contents, or photoactive medical diagnostic markers. Also, through analysis of eye tone, a variety of eye maladies may be detected directly or indirectly.

Accordingly, the optical computing devices of the present disclosure provide a number of advantages. First, for example, the devices allow remote diagnoses and early treatment of medical issues. Second, the devices may be utilized with computer networks or mobile computing technology for integrated diagnosis. Third, the quality of disease management may be improved because medical emergencies may be detected earlier. Fourth, the devices may be used in emergency situations to start treatment while confirmation is sought via standard lab procedures. Fifth, the robustness of RDT devices is improved because of the increased sensitivity of analysis provided by optical computing devices.

Embodiments described herein further relate to any one or more of the following paragraphs:

1. A method for medical monitoring utilizing an optical computing device, the method comprising optically interacting electromagnetic radiation with a sample to produce sample-interacted light; and optically interacting the sample-interacted light with a multivariate optical calculation device forming part of the optical computing device, the multivariate optical calculation device being positioned to perform a regression calculation on the sample-interacted light to thereby produce a signal which corresponds to at least one medical characteristic of the sample.

2. An optical computing method as defined in paragraph 1, wherein the method is utilized to perform an antigen-based rapid diagnostic test ("RDT").

3. An optical computing method as defined in any of paragraphs 1-2, wherein the sample is blood, urine, stool, skin or an eye; and the signal corresponding to the medical characteristic indicates the presence of allergens, parasites, diseases, sugars, enzymes, proteins, or drugs.

4. An optical computing method as defined in any of paragraphs 1-3, further comprising communicating an alert signal based upon the signal that corresponds to the medical characteristic of the sample.

5. An optical computing method as defined in any of paragraphs 1-4, further comprising communicating the alert signal as a visual or audible alert.

6. An optical computing method as defined in any of paragraphs 1-5, wherein the optical computing device forms part of a portable device having a display, the method further comprising optically interacting the sample-interacted light with an Integrated Computational Element ("ICE") core positioned within the multivariate optical calculation device to produce optically-interacted light, the ICE core being configured to be associated with the medical characteristic of the sample; detecting the optically-interacted light with a detector and thereby generating the signal corresponding to the medical characteristic of the sample; and displaying data related to the medical characteristic on the display.

7. An optical computing method as defined in any of paragraphs 1-6, wherein the optical computing device forms part of a viewing device having viewing optics, the method further comprising optically interacting the sample-interacted light with an Integrated Computational Element ("ICE") positioned along the viewing optics; and filtering the sample-interacted light using the ICE such that an optical signature of the sample is visible through the viewing optics, the ICE being configured to be associated with the medical characteristic of the sample.

8. An optical computing method as defined in any of paragraphs 1-7, wherein the viewing device form part of a portable device, fiber probe or facial glasses.

9. An optical computing method as defined in any of paragraphs 1-8, wherein the optical computing device forms part of a dialysis machine; and the sample is blood.

10. An optical computing method as defined in any of paragraphs 1-9, wherein the optical computing device forms part of a breathalyzer machine, the sample being breathe particles.

11. An optical computing method as defined in any of paragraphs 1-10, wherein the optical computing device hums part of a skin analysis device, the method further comprising optically interacting the electromagnetic radiation with skin to produce the sample-interacted light; optically interacting the sample-interacted light with an Integrated Computational Element ("ICE") core positioned within the multivariate optical calculation device to produce optically-interacted light, the ICE core being configured to be associated with the medical characteristic of the sample; and detecting the optically-interacted light with a detector and thereby generating the signal corresponding to the medical characteristic of the sample.

12. An optical computing method as defined in any of paragraphs 1-11, wherein the sample is skin or blood within the skin.

13. An optical computing method as defined in any of paragraphs 1-12, wherein the optical computing device is worn on the skin.

14. An optical computing method as defined in any of paragraphs 1-13, further comprising determining whether the RDT is temperature damaged using the multivariate optical calculation device.

15. An optical computing method as defined in any of paragraphs 1-14, further comprising determining whether the RDT is water damaged using the multivariate optical calculation device.

16. An optical computing method as defined in any of paragraphs 1-15, wherein the medical characteristic is corrected for a presence of a chemical interferent in the sample, the method further comprising optically interacting the sample-interacted light with an ICE core positioned within the multivariate optical calculation, the ICE core being configured to be associated with the medical characteristic of the sample; filtering the chemical interferent from the sample-interacted light to thereby produce optically-interacted light; and detecting the optically-interacted light with a detector and thereby generating the signal corresponding to the medical characteristic of the sample.

17. An optical computing device to perform any of the methods defined in paragraphs 1-16.

18. An optical computing device utilized for medical monitoring, the device comprising a housing and a multivariate optical calculation device positioned inside the housing to perform a regression calculation on sample-interacted light to thereby produce a signal which corresponds to at least one medical characteristic of a sample.

19. An optical computing device as defined in paragraph 18, further comprising a display to display data related to the medical characteristic; or a mechanism to generate an alert signal corresponding to the medical characteristic.

20. An optical computing device as defined in any of paragraphs 18-19, wherein the housing is handheld; and the multivariate optical calculation device comprises one or more channels in which to place the sample; an electromagnetic radiation source to produce light which optically interacts with the sample positioned within the channel to generate the sample-interacted light; an Integrated Computational Element ("ICE") core positioned to optically interact with the sample-interacted light to thereby produce optically-interacted light, the ICE core being associated with the medical characteristic of the sample; and a detector positioned to measure the optically-interacted light and thereby generate a signal utilized to determine the medical characteristic of the sample.

21. An optical computing device as defined in any of paragraphs 18-20, wherein the sample is placed on a testing strip positioned along the one or more channels.

22. An optical computing device as defined in any of paragraphs 18-21, wherein the housing comprises a viewing optic through which to view the sample and an indicator of the medical characteristic; and the multivariate optical calculation device positioned along the viewing optic, the multivariate optical calculation device comprising an Integrated Computational Element ("ICE") core positioned to optically interact with sample-interacted light to thereby produce optically-interacted light to be viewed by a human eye, the ICE core being associated with the medical characteristic of the sample.

23. An optical computing device as defined in any of paragraphs 18-22, wherein the viewing optic forms part of facial glasses; or the viewing optic forms part of a handheld device.

Although various embodiments and methodologies have been shown and described, the disclosure is not limited to such embodiments and methodologies and will be understood to include all modifications and variations as would be apparent to one skilled in the art. For example, it is not necessary that the computing device be microfluidic, as other embodiments of the present disclosure may be embodied in non-microfluidic systems. Therefore, it should be understood that the disclosure is not intended to be limited to the particular forms disclosed. Rather, the intention is to cover all modifications, equivalents and alternatives falling within the spirit and scope of the disclosure as defined by the appended claims.

What is claimed is:

1. A method for medical monitoring utilizing an optical computing device, the method comprising:
   optically interacting electromagnetic radiation with a sample to produce sample-interacted light;
   optically interacting the sample-interacted light with a multivariate optical calculation device forming part of the optical computing device, the multivariate optical calculation device having an Integrated Computational Element ("ICE") core and being positioned to perform a regression calculation on the sample-interacted light to thereby produce a signal which corresponds to at least one medical characteristic of the sample;
   determine at least one medical characteristic of the sample using the signal, wherein the optical computing device is an antigen-based rapid diagnostic test ("RDT") device;
   determine, using the multivariate optical calculation device, whether the antigen-based RDT device is temperature damaged or water damaged; and
   responsive to a determination the antigen-based RDT device is temperature or water damaged, correcting the signal.

2. An optical computing method as defined in claim 1, wherein:
   the sample is food; and
   the signal corresponding to the medical characteristic indicates the presence of allergens or sugars.

3. An optical computing method as defined in claim 1, further comprising communicating an alert signal based upon the signal that corresponds to the medical characteristic of the sample.

4. An optical computing method as defined in claim 3, further comprising communicating the alert signal as a visual or audible alert.

5. An optical computing method as defined in claim 1, wherein the optical computing device forms part of a portable device having a display, the method further comprising:
   optically interacting the sample-interacted light with the ICE core positioned within the multivariate optical calculation device to produce optically-interacted light, the ICE core being configured to be associated with the medical characteristic of the sample;

detecting the optically-interacted light with a detector and thereby generating the signal corresponding to the medical characteristic of the sample; and displaying data related to the medical characteristic on the display.

6. An optical computing method as defined in claim 1, wherein:

the optical computing device forms part of a dialysis machine; and the sample is blood.

7. An optical computing method as defined in claim 1, wherein the optical computing device forms part of a breathalyzer machine, the sample being breathe particles.

8. An optical computing method as defined in claim 1, wherein the optical computing device forms part of a skin analysis device, the method further comprising:

optically interacting the electromagnetic radiation with skin to produce the sample-interacted light;

optically interacting the sample-interacted light with the ICE core positioned within the multivariate optical calculation device to produce optically-interacted light, the ICE core being configured to be associated with the medical characteristic of the sample; and detecting the optically-interacted light with a detector and thereby generating the signal corresponding to the medical characteristic of the sample.

9. An optical computing method as defined in claim 8, wherein the sample is skin or blood within the skin.

10. An optical computing method as defined in claim 9, wherein the optical computing device is worn on the skin.

11. An optical computing device to perform the method of claim 1.

12. An optical computing device utilized for medical monitoring, the device comprising:

a housing; and a multivariate optical calculation device inside the housing having an Integrated Computational Element ("ICE") core and positioned to perform a regression calculation on sample-interacted light to thereby produce a signal which corresponds to at least one medical characteristic of a sample, wherein at least one medical characteristic of the sample is determined using the signal, wherein the optical computing device is an antigen-based rapid diagnostic test ("RDT") device, and wherein the optical computing device determines, using the multivariate optical calculation device, whether the antigen-based RDT device is temperature damaged or water damaged and responsive to a determination the antigen-based RDT device is temperature or water damaged, correcting the signal.

13. An optical computing device as defined in claim 12, further comprising:

a display to display data related to the medical characteristic; or a mechanism to generate an alert signal corresponding to the medical characteristic.

14. An optical computing device as defined in claim 12, wherein:

the housing is handheld; and the multivariate optical calculation device comprises:

one or more channels in which to place the sample;

an electromagnetic radiation source to produce light which optically interacts with the sample positioned within the channel to generate the sample-interacted light;

the ICE core positioned to optically interact with the sample-interacted light to thereby produce optically-interacted light, the ICE core being associated with the medical characteristic of the sample; and a detector positioned to measure the optically-interacted light and thereby generate a signal utilized to determine the medical characteristic of the sample.

15. An optical computing device as defined in claim 12, wherein the sample is placed on a testing strip positioned along the one or more channels.

16. An optical computing device as defined in claim 12, wherein:

the housing comprises a viewing optic through which to view the sample and an indicator of the medical characteristic; and the multivariate optical calculation device positioned along the viewing optic, the multivariate optical calculation device comprising the ICE core positioned to optically interact with sample-interacted light to thereby produce optically-interacted light to be viewed by a human eye, the ICE core being associated with the medical characteristic of the sample.

17. An optical computing device as defined in claim 16, wherein the viewing optic forms part of facial glasses.

* * * * *